US012751657B2

(12) United States Patent
Fabregat Sanjuan et al.

(10) Patent No.: US 12,751,657 B2
(45) Date of Patent: Oct. 6, 2026

(54) ELECTRODE DEVICE FOR AMPLITUDE-INTEGRATED ELECTROENCEPHALOGRAPHY

(71) Applicants: UNIVERSITAT ROVIRA I VIRGILI, Tarragona (ES); INSTITUT D'INVESTIGACIÓ SANITÀRIA PERE VIRGILI, Tarragona (ES)

(72) Inventors: Albert Fabregat Sanjuan, Tarragona (ES); Vicenç Pascual Rubio, Tarragona (ES)

(73) Assignees: UNIVERSITAT ROVIRA I VIRGILI, Tarragona (ES); INSTITUT D'INVESTIGACIÓ SANITÀRIA PERE VIRGILI, Tarragona (ES)

( * ) Notice: Subject to any disclaimer, the term of this patent is extended or adjusted under 35 U.S.C. 154(b) by 538 days.

(21) Appl. No.: 17/919,846

(22) PCT Filed: Apr. 19, 2021

(86) PCT No.: PCT/EP2021/060103

§ 371 (c)(1),
(2) Date: Oct. 19, 2022

(87) PCT Pub. No.: WO2021/213985

PCT Pub. Date: Oct. 28, 2021

(65) Prior Publication Data

US 2023/0144282 A1 May 11, 2023

(30) Foreign Application Priority Data

Apr. 20, 2020 (EP) .................................... 20382317

(51) Int. Cl.
*A61B 5/257* (2021.01)
*A61B 5/00* (2006.01)
(Continued)

(52) U.S. Cl.
CPC .............. *A61B 5/257* (2021.01); *A61B 5/263* (2021.01); *A61B 5/291* (2021.01); *A61B 5/6814* (2013.01)

(58) Field of Classification Search
CPC ......... A61B 5/257; A61B 5/263; A61B 5/291; A61B 5/6814
See application file for complete search history.

(56) References Cited

U.S. PATENT DOCUMENTS 4,029,086 A 6/1977 Corasanti
4,166,457 A * 9/1979 Jacobsen ................ A61B 5/324 600/397

(Continued)

FOREIGN PATENT DOCUMENTS

CN 107788976 A 3/2018
FR 2400370 A1 3/1979

(Continued)

*Primary Examiner* — Joseph A Stoklosa
*Assistant Examiner* — William Mossbrook
(74) *Attorney, Agent, or Firm* — The Webb Law Firm

(57) ABSTRACT

An electrode device for aEEG is disclosed. The electrode device includes a housing mounted on an adhesive element to adhere the electrode device to a skin surface of a patient; an electrode plate placed in the housing; and a wire connection for the electrode plate. The housing has a first protruding part that includes a conical-shaped hole for injecting and removing an electroconductive gel and that is disposed in the housing inclined outwardly at an angle between 50 degree and 80 degree with respect to the longitudinal direction of the skin surface. The housing also has a second protruding part that includes a hole for the introduction of the wire connection in order to be attached to the electrode plate. The second protruding part is disposed on the axis of the housing

17 Claims, 10 Drawing Sheets

(51) Int. Cl.

| | |
|---|---|
| ***A61B 5/263*** | (2021.01) |
| ***A61B 5/291*** | (2021.01) |

(56) References Cited

U.S. PATENT DOCUMENTS

| | | | | | |
|---|---|---|---|---|---|
| 4,250,878 | A * | 2/1981 | Jacobsen | A61N 1/0444 604/20 |
| 4,657,023 | A | 4/1987 | Kuhn | |
| 4,968,297 | A | 11/1990 | Jacobsen et al. | |
| 5,037,380 | A * | 8/1991 | Jacobsen | A61N 1/0448 604/20 |
| 5,087,241 | A * | 2/1992 | Mathiesen | A61N 1/044 604/20 |
| 2007/0225585 | A1* | 9/2007 | Washbon | A61B 5/291 600/383 |
| 2014/0206976 | A1* | 7/2014 | Thompson | A61B 5/25 600/391 |
| 2017/0127969 | A1* | 5/2017 | Su | A61B 5/288 |
| 2019/0053730 | A1* | 2/2019 | Williams | A61B 5/6868 |

FOREIGN PATENT DOCUMENTS

| | | | |
|---|---|---|---|
| JP | S5922109 | U | 2/1984 |
| JP | H3114476 | A | 5/1991 |
| JP | H11513592 | A | 11/1999 |
| JP | 2002209864 | A | 7/2002 |
| WO | 9714358 | A1 | 4/1997 |

* cited by examiner

ELECTRODE DEVICE FOR AMPLITUDE-INTEGRATED ELECTROENCEPHALOGRAPHY

CROSS-REFERENCE TO RELATED APPLICATIONS

This application is the United States national phase of International Application No. PCT/EP2021/060103 filed Apr. 19, 2021, and claims priority to European Patent Application No. 20382317.4 filed Apr. 20, 2020, the disclosures of which are hereby incorporated by reference in their entirety.

BACKGROUND OF THE DISCLOSURE

Field of the Disclosure

The present disclosure is directed, in general, to the field of medical electrodes. In particular, the disclosure relates to an electrode device designed to record superficial brain bioelectric activity during long periods of time from infants in the neonatal intensive care units (NICU's). The electrode is particularly designed to be used in amplitude-integrated electroencephalography (aEEG), however it can also be used to record other long-term neurophysiological recording tests such as continuous electroencephalography monitoring (CEEG), among others.

Description of Related Art

Amplitude-integrated electroencephalography (aEEG) is an easily accessible technique for monitoring the brain function in infants. In its simplest form, aEEG is a processed single-channel electroencephalogram that is filtered, rectified, enlarged with a semilogarithmic scale and time compressed.

There are several specific technical aspects for infant aEEG in the NICUs to be considered, beginning with the montage and electrode placement, the long-term recordings (several days or weeks), the lying position of the infants in the NICUs, the frequent manipulation by healthcare staff, the characteristic morphology of the head and the fragility of the scalp of preterm and term infants.

The known or commercial electrodes do not fulfill the requirements needed for infants and present artifacts in the electrical neuroactivity readings. For infants in a critical situation puts risk relevant clinical decisions.

The current problem is not well tackled as the available surface electrodes are not properly sized for term and preterm infant's application. Also, they are usually attached to a long wire that connects them to the bioelectric signal amplifier. This long wire electrode hinders the manipulation of the newborn by health care staff. In addition, the electrode wire is usually attached to the electrode laterally. In the lying patient, the usual position in the NICU's, this joint causes a lever force that facilitates the electrode decoupling.

Superficial cup electrodes available have a hole through which the electroconductive gel is replaced in order to maintain its high conductive capacity during long-term recordings. During this process, a blunt-tipped syringe is usually used to remove the old electroconductive gel and apply the new one. At this time, it is usually necessary to apply vertical pressure to beat the conductive gel layer that may have dried on the long-term recordings. This pressure can cause an involuntary contact with the scalp surface, which should be avoided in newborns due to their fragility and proximity to the fontanelles. Also, its rigid consistency (gold or silver electrodes) causes that when they are fixed with adherent tape, the skin indemnity can be put at risk, as well as, the electrodes cover the recording site not offering the opportunity to check the skin of the newborn without detach the electrode.

Disposable adhesive electrodes have the disadvantage of not allowing the replacement of the electroconductive gel and therefore they must be replaced periodically. This involves more manipulation and possible changes in the recording conditions (placement, impedance, etc.), in a situation where a constant monitorization without cuts is a key element.

The subdermal needle electrodes which are often used in the aEEG to achieve low impedance recordings have the disadvantage of producing pain. Pain should always be avoided to improve comfort but in the aEEG it also has the disadvantage of not allowing the accurate assessment of a parameter as important as the latency of onset of the sleep-wake cycle. In addition, the subdermal electrodes have the same drawbacks as most surface electrodes available: are connected to a long wire to the amplifier and are easily detached.

There are known some patents and patents applications in this field.

FR2400370 discloses an electrode device intended to be applied to the skin, for electro-medical purposes. The electrode device can be used for electroencephalography, electrocardiography and electromyography. The electrode comprises a plastics body with a ring-shaped surface that is stuck to the skin by a double-sided tape. An electrode is arranged in a cavity that can be filled with a conductive paste or gel through a hole. The hole is arranged on the axis of the electrode body. At least one discharge duct from the cavity is provided for excess paste or gel, preferably in the form of a groove in the electrode body under the adhesive tape. This electrode has the disadvantage of having the long cable making it difficult for the healthcare staff to handle the child. The connection between the plate and the cable is lateral, facilitating the uncoupling of the electrode by lever forces in the lying patient. Moreover, this type of electrode device does not avoid the possible contact with the scalp during the replacement of electroconductive gel.

U.S. Pat. No. 4,657,023-A provides a self-adhering electrode for application on the skin of a patient in which a portion of the electrically conductive layer forms an electrode that is substantially surrounded by a pressure-sensitive layer and the remainder of the conductive layer is covered by a substrate which is also conductive and sufficiently pliant to permit the electrode to adjust to the body contour. This electrode does not allow electrode conductive gel replacement without removing the electrode. It has a long wire laterally connected that complicates the manipulation of the infant and facilitates the uncoupling of the electrode by lever forces in the lying patient.

U.S. Pat. No. 4,029,086-A provides an electrode arrangement which provides for a reliable electrical contact with the skin of a person or animal. The electrode arrangement comprises, in combination, a central post with a base flange, an adhesive pad having a central aperture for receiving the central post, a gel member and a resilient o-ring shaped member. An alternate embodiment comprises a central post and base flange, an adhesive pad having a central aperture for receiving the central post, and a shield washer, with a central aperture for receiving the central post, mounted above the adhesive pad. Both embodiments minimize the effect of physical forces placed on the electrical contact. This electrode has the same disadvantages as U.S. Pat. No. 4,657,023-A.

U.S. Pat. No. 4,166,457-A discloses a dry-state bioelectrode having a self-sealing receptacle for receiving electrolyte and/or medicament fluid contents. The receptacle is attached at its opening to a sheet-like flexible base member having an opening in common with the receptacle opening, the bottom of the base member being adapted for fixation at a skin surface. A portion of the skin surface is exposed to the fluid contents of the receptacle through the common opening. An injection site communicates through the wall of the receptacle and provides controlled access for filling. Upon completion of filling, the receptacle self-seals, retaining the fluid contents therein for application of iontophoresis treatment or other procedures requiring use of a potential gradient. An electrode plate is supported at an interior surface of the receptacle for supplying the desired electric potential. This bioelectrode does not have a first protruding part arranged inclined at an angle between 50-80° with respect to the contact surface of the bioelectrode (i.e. the surface of the bioelectrode contacting the skin surface of the patient).

For at least these reasons, a new electrode device which solves the problems of current electrodes is needed.

SUMMARY OF THE DISCLOSURE

To that end, the present disclosure proposes, according to one aspect, an electrode device for aEEG. As known in the field, the electrode device comprises a housing fixed on an adhesive element to adhere the electrode device to the skin surface of a patient, particularly the scalp; an electrode plate placed in the housing at a certain distance from a support surface of the housing forming a hollow space; and a wire connection for the electrode.

The housing has two protruding parts, a first protruding part and a second protruding part. The first protruding part includes or provides a first hole. The second protruding part includes or provides a second hole for the introduction of the wire connection, so that the wire connection can be attached, e.g. by means of one or more welding points, to the electrode plate. The second protruding part can also have the function of allowing the flow of the electroconductive gel from the hollow space between the electrode plate and the skin to the exterior of the housing to drain the gel from first protruding part to the second one. The second protruding part is disposed, substantially, on the axis of the housing. Therefore, the wire connection is maintained perpendicular or almost perpendicular (about90°) to the skin surface when performing the measures, which allows minimizing the tangential forces that favor the inclination of the electrode plate and it's uncoupling from the scalp. Likewise, the electrode plate is placed horizontally (i.e. flat or parallel, or substantially parallel, to the skin surface, e.g. the brain's cortex) inside the housing. Hence, the sum of the postsynaptic potentials of the different pyramidal neurons oriented vertically to the brain cortex will be captured homogeneously by means of the whole surface of the electrode plate.

The first hole has a conical shape for injecting and replacing an electroconductive gel inside the hollow space. The first protruding part is disposed in the housing inclined outwardly at an angle between 50-degree and 80-degree with respect to the contact surface of the electrode device (i.e. the bottom surface of the electrode device contacting the skin surface of the patient).

The proposed electrode device has a size and form adaptable to the head of a newborn. It is connected with a short wire that, once disconnected from an amplifier, facilitates the manipulation of the infant by the healthcare staff. The vertical orientation of the insertion between the electrode plate and the wire improves stability in the lying position. The conical hole prevents accidental contact of a blunt tip of a needle with the infant's scalp and allows the safe replacement of the electroconductive gel, thus facilitating the good signal quality during long-term recordings. Furthermore, by being a surface electrode, it does not cause discomfort to the patient.

In an embodiment, the electrode plate comprises a first gap which allows the electroconductive gel to flow through and a second gap to fix the rotating position of the electrode plate to the housing using a clamping element. Hence the distance between the skin surface and the electrode plate is reduced (i.e. the mentioned hollow space is smaller).

In a particular embodiment, the first protruding part is disposed at a 60-degree angle with respect to the contact surface of the electrode device.

The first protruding part can include a plug for closure of the first hole. Hence, the properties of the electroconductive gel can be kept for a longer period of time.

The housing can be made of a polymer, ceramic or metallic material. In a particular embodiment, the housing is made of a thermoplastic Polyether-Polyurethane elastomer. The electrode plate can be made of, or can comprise a coating made of, Silver (Ag), Gold (Au), Silver/Silver-Chloride (Ag/AgCl), or any good electrical conductor material (e.g. Tin, Stainless Steel, Platinum, Cooper, Lead, or Nichrome). In other embodiments, the electrode plate can be made of, or can comprise a coating made of, a conductive polymer such Liquid Cristal Polymer (LCP), Polyether ether ketone (PEEK), Polyphenylsulfone (PPSU, PPSF), ultra-high molecular weight polyethylene, among others; therefore the electrode is fully MRI-compatible. In any case, for the electrode being fully MRI-compatible any conductive and non-magnetic material can be used.

In yet other embodiments, the electrode besides being fully MRI-compatible can be also radiolucent. In this particular case the wire is preferably made of one or more carbon fibers.

In an embodiment, the adhesive element is a flexible adhesive pad including an adhesive layer provided on a lower or bottom surface of the adhesive element. Alternatively or complementarily, the adhesive element comprises a double-sided tape.

In an embodiment, the electrode device also has a connector such as a touchproof connector or a male snap connector, among others, arranged on a distal end of the wire connector.

In an embodiment, the length of the wire connection is less than 50 millimeters, particularly of approximately 30 millimeters. In other embodiments, the length of the wire connection is between 50 millimeters and 600 millimeters, preferably 100 millimeters. In yet other embodiments, the length of the wire connection can be between 0.6 and 2 meters.

In some embodiments, the wire connection can have a spiral/curved shape in order to have an elastic behavior that will absorb some axial force from the wires of a bioelectric signal amplifier.

In some embodiments, the wire connection can also include an insulating layer, for example made of a material comprising silicone, Polyvinyl chloride, Polypropylene, Polyethylene, XLPE (Cross-Linked Polyethylene), EPR (Ethylene Propylene Rubber), ECTFE (ethylene chlorotrifluoroethylene), PVDF (Polyvinylidene fluoride), Nylon, CPE (Chlorinated polyethylene), etc.

In yet some embodiments, one or more sealing elements can be disposed between the housing and the insulating layer of the wire connection and/or over the housing and the first protruding part/first hole.

In an embodiment, the surface of the housing in contact with the adhesive element has a curvature that better fits with the skull shape.

In some embodiments, the electrode plate support surface is formed by several supports that sustain the electrode plate horizontally disposed (i.e. parallel or substantially parallel to the skin surface of the patient). In addition, the electrode device also includes an encapsulating/isolation element positioned on top of the electrode plate. The encapsulating element prevents the gel from contacting the wire connection, thus avoiding galvanic corrosion.

In some embodiments, the electrode device comprises a third protruding part that is symmetrically arranged with regard to the first protruding part. The third protruding part has also a conical-shaped hole particularly for replacing the electroconductive gel present in the hollow space.

Hence, the proposed electrode device allows an easy electrode placement as well as a wire cable extension that permits an easier electrical connection. The electrode device design also allows the patient, in particular newborns, to rotate the head without difficulties. The new design allows replacing the electroconductive gel for long-term aEEG recordings.

BRIEF DESCRIPTION OF THE DRAWINGS

The previous and other advantages and features will be more fully understood from the following detailed description of embodiments, with reference to the attached figures, which must be considered in an illustrative and non-limiting manner, in which:

FIG. 4B is an enlarged view of section B outlined in FIG. 4A.

DETAILED DESCRIPTION OF THE DISCLOSURE

Figure 1A:
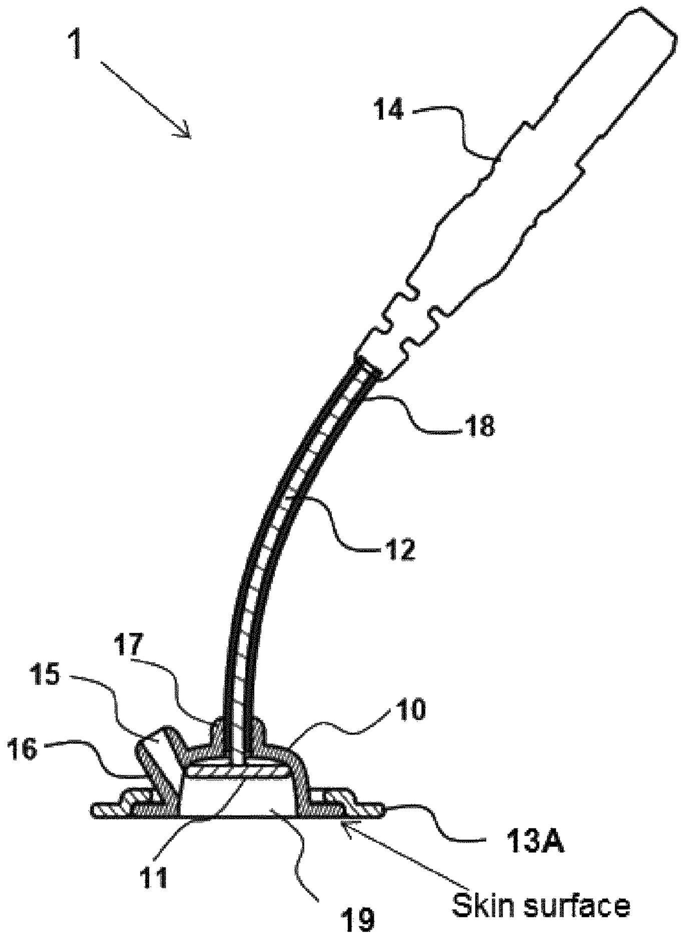
FIGS. 1A-1C illustrate different views of the proposed electrode device, according to an embodiment of the present disclosure.
Figure 1B:
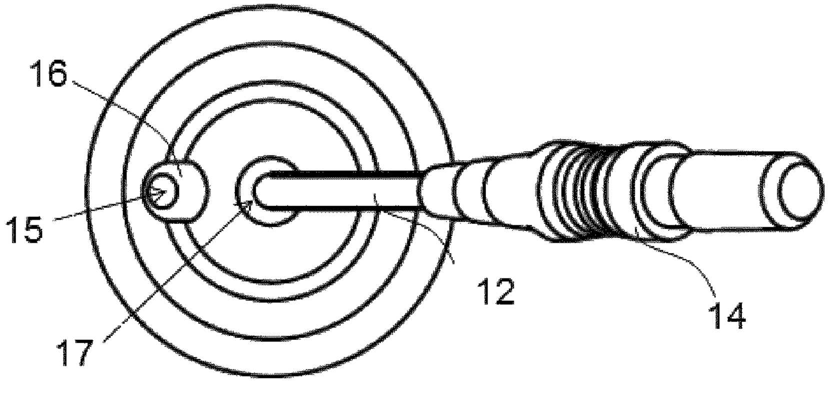
Figure 1C:
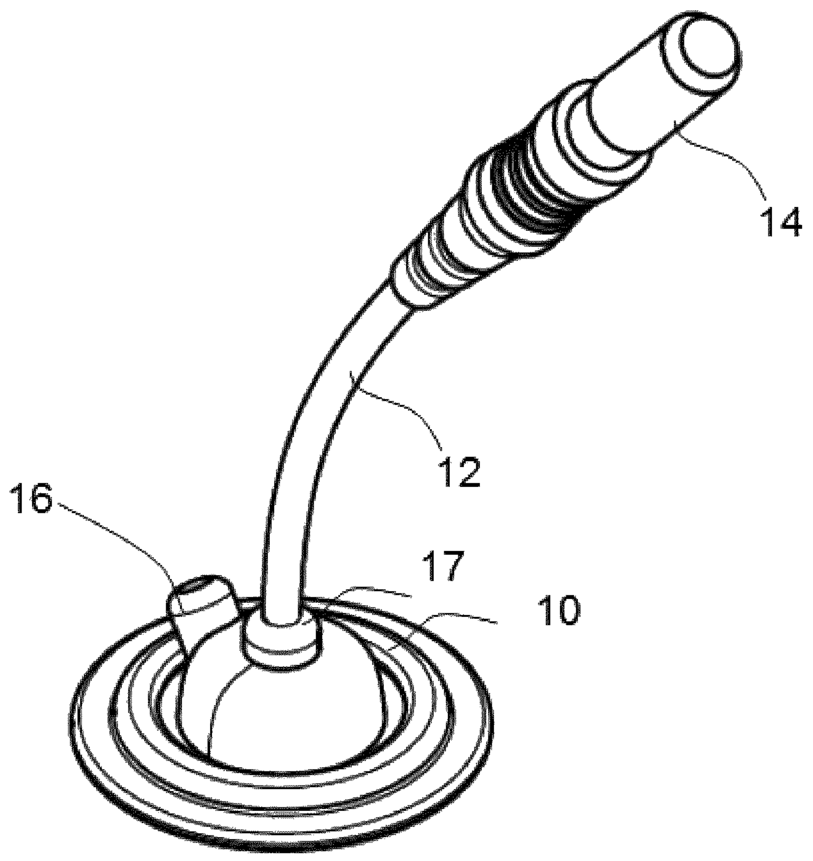

With reference to FIGS. 1A-1C, therein a first embodiment of the proposed electrode device is showed. The electrode device 1 of this embodiment includes a housing 10, for example made of a polymeric, ceramic or metallic material, which is mounted or arranged on a flexible adhesive pad 13A to adhere the electrode device 1 to a skin surface of a patient. The flexible adhesive pad 13A has an adhesive layer provided on a lower/bottom surface thereof to allow said adhesion of the electrode device 1 to the skin surface. As seen in the figures, the flexible adhesive pad 13A has a larger diameter than the housing 10.

The electrode device 1 also includes an electrode plate 11 horizontally disposed (i.e. parallel or substantially parallel to the skin surface of the patient) inside the housing 10 at a certain distance therein forming a hollow space 19. In particular, the electrode plate 11 is made of, or comprises a coating made of, Silver (Ag), Gold (Au), or Silver/Silver-Chloride (Ag/AgCl). In other embodiments however any other good electrical conductor material such as Tin, Stainless Steel, Platinum, Cooper, Lead, or Nichrome, among others, can be used. In some other embodiments, the electrode device 1 is fully MRI-compatible and/or radiolucent. In this case, conductive and non-magnetic materials should be used for the electrode plate 11 and/or wire connection 12.

Also, the electrode device 1 includes a flexible wire connection 12 for the electrode plate 11. The wire connection 12 is fixed to the electrode plate 11 by one of its extremes using at least one welding point, the other extreme being attached to a touchproof connector 14. It should be noted that in other embodiments, in this case not illustrated, the connector used can be of different type, for example a male snap connector, among others. Likewise, it should be noted that in other embodiments, an adhesive element comprising a double-sided tape 13B (see FIG. 3 and FIGS. 4A and 4B for example) can be used instead of the flexible adhesive pad 13A. In yet other embodiments, the adhesive element comprises a hydrocolloid adhesive; thus the electrode device 1 is for single-patient use and it is disposable.

In some embodiments, the housing 10 is translucent and flexible. By being translucent skin check (irritation), gel check (from drying or spilling) and electrode plate check (from movements or change in color for checking the Ag/AgCI coating, corrosion . . . ) are easily possible. By being flexible a better interaction with the skin is further enabled (skin injures due to the reduction to stress concentrations caused by rigid materials is avoided).

The housing 10 has two protruding parts 16, 17. In this particular embodiment, the first protruding part 16 is located inclined outwardly at an angle of approximately 60°-65° with regard to the longitudinal direction of the skin surface (or with regard to the contact surface of the electrode device 1). It should be noted that in other embodiments, in this case not illustrated, the first protruding part 16 can be located at an angle between 50° and 80° with respect to the contact surface of the electrode device 1. The first protruding part 16 includes a conical-shaped hole 15 to allow the injection and removal of an electroconductive gel or hydrogel. The second protruding part 17 is located about the axis of the housing 10 and includes a second hole for the upright introduction of the wire connection 12.

Any biocompatible electroconductive gel can be used in accordance with the present disclosure. The electroconductive gel can be replaced via a blunt needle through the conical-shaped hole 15 but the needle is blocked by the geometry of the hole to avoid skin injuries.

Particularly, the electrode device 1 of FIGS. 1A-1C also includes an insulting layer 18 surrounding the wire connection. Different materials can be used as insulating layer for example silicone, Polyvinyl chloride, Polyethylene, Polyvinylidene fluoride and/or Polypropylene, among others.

Figure 2A:
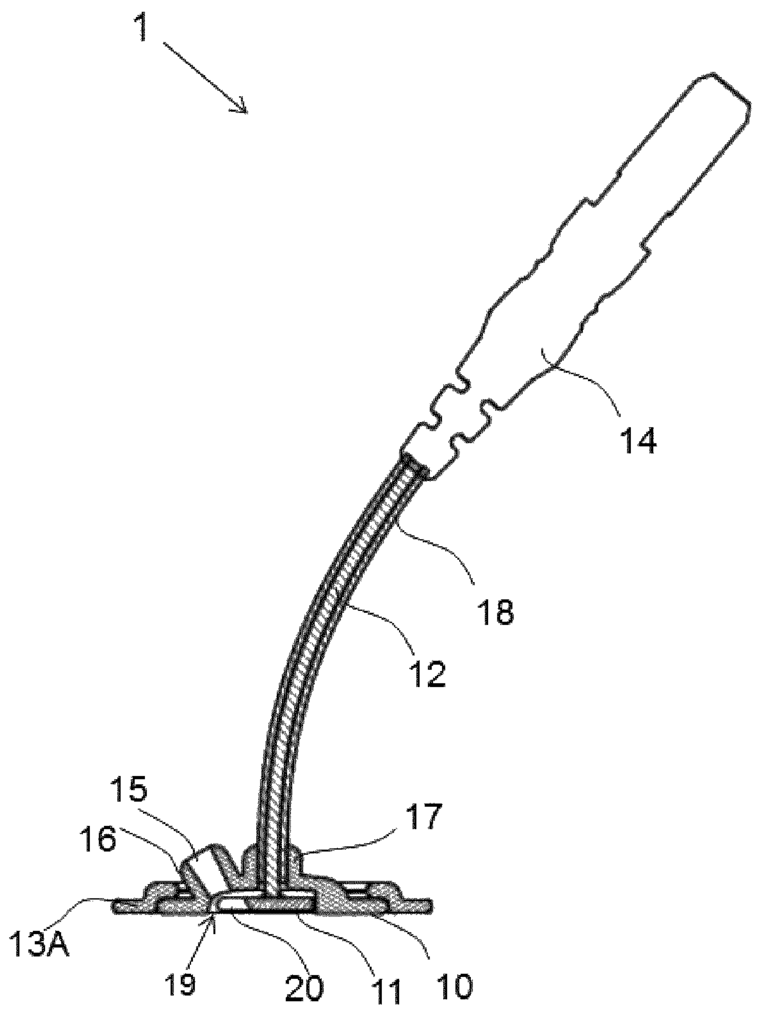
FIGS. 2A-2C illustrate different views of another embodiment of the proposed electrode device.
Figure 2B:
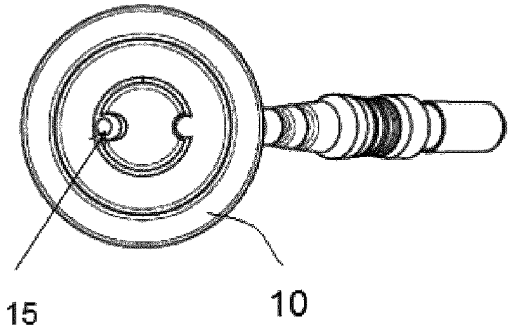
Figure 2C:
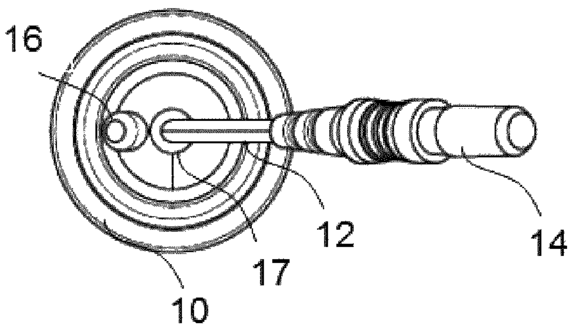

With regard to FIGS. 2A-2C, therein another embodiment of the proposed electrode device 1 is illustrated. In this case, different to the embodiment of FIGS. 1A-1C, the hollow space 19 is reduced since the electrode plate 11 is pierced in two parts: one opening 20 is disposed to fit with the conical-shaped hole 15 to allow the electroconductive gel to flow through; the other opening (not seen in the figures) is used for the fixation of the electrode plate 11 to the housing 10, for example via a clamping or fixing element.

Figure 3:
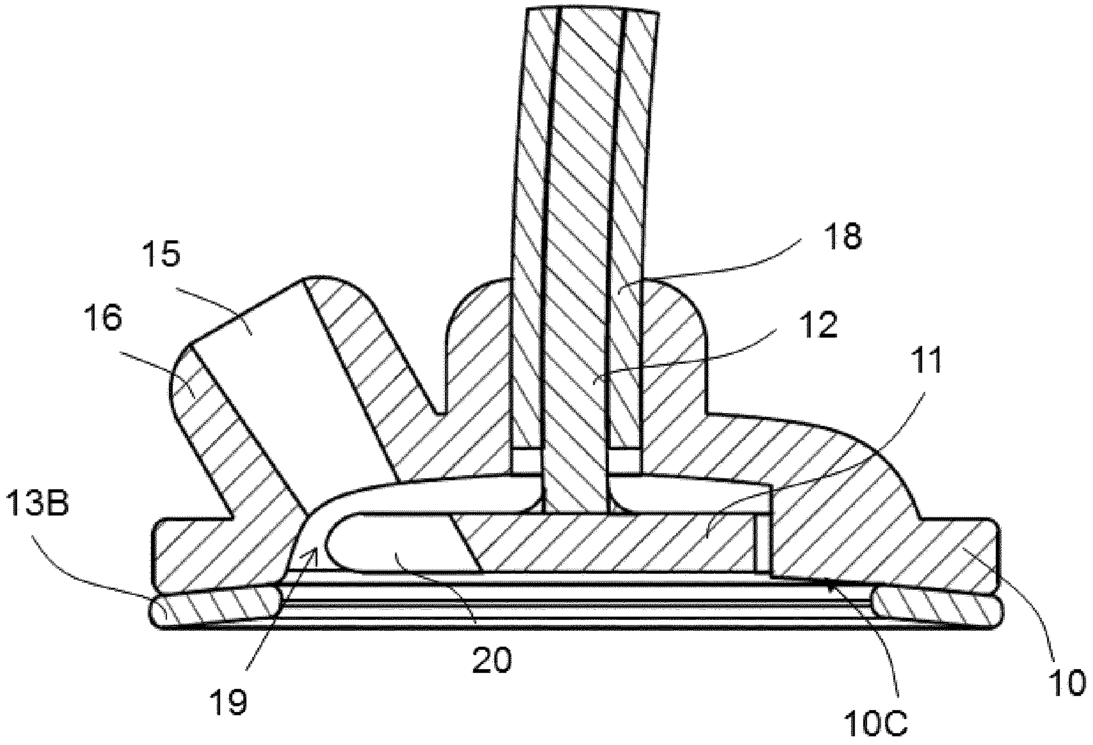
FIG. 3 illustrates another embodiment of the proposed electrode device. In this case, the surface of the housing configured to contact the adhesive element is curved. The adhesive element comprises a double-sided tape.

FIG. 3 illustrates an embodiment in which a bottom surface 10C of the housing 10 that contacts the adhesive element comprises a curvature to better fit with the skull. The size of the housing 10 in this case is reduced. In this embodiment, particularly, the adhesive element comprises a double-sided tape 13B.

Figure 4A:
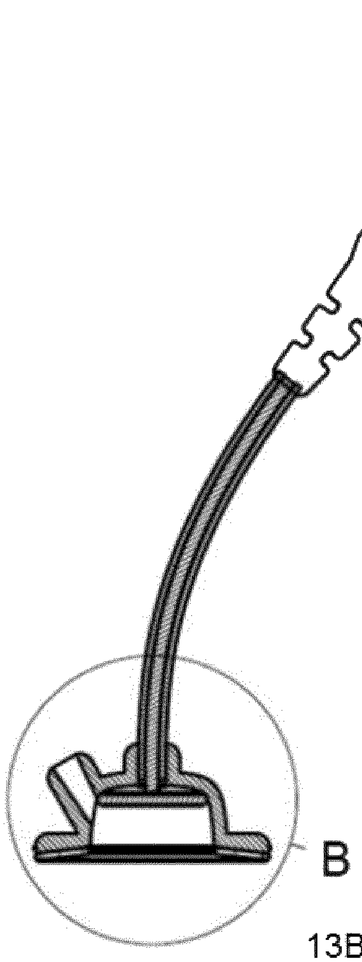
FIGS. 4A-4B illustrate another embodiment of the proposed device in which the surface of the housing configured to contact the adhesive element is curved. In this case the adhesive element comprises a double-sided tape.
Figure 4B:
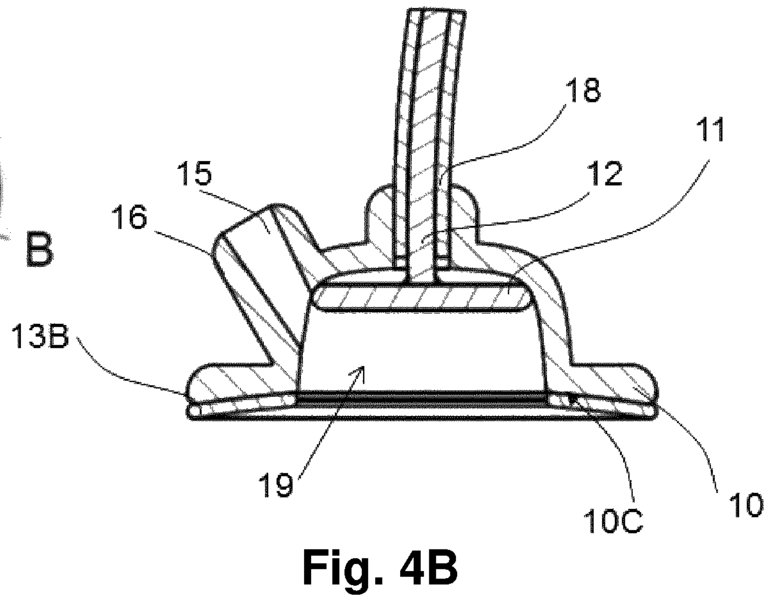
Figure 5A:
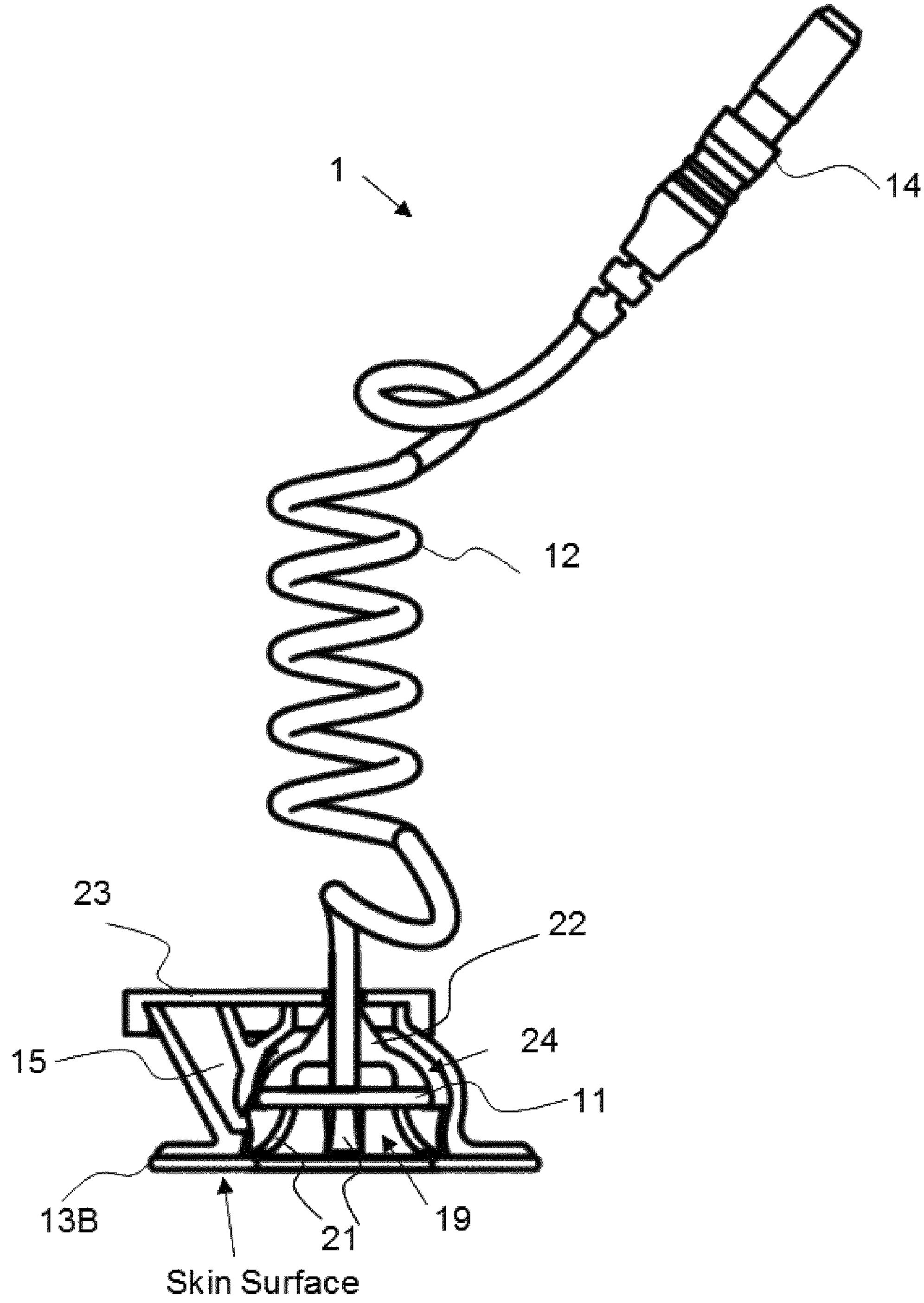
FIGS. 5A-5E illustrate different views of another embodiment of the proposed electrode device.
Figure 5B:
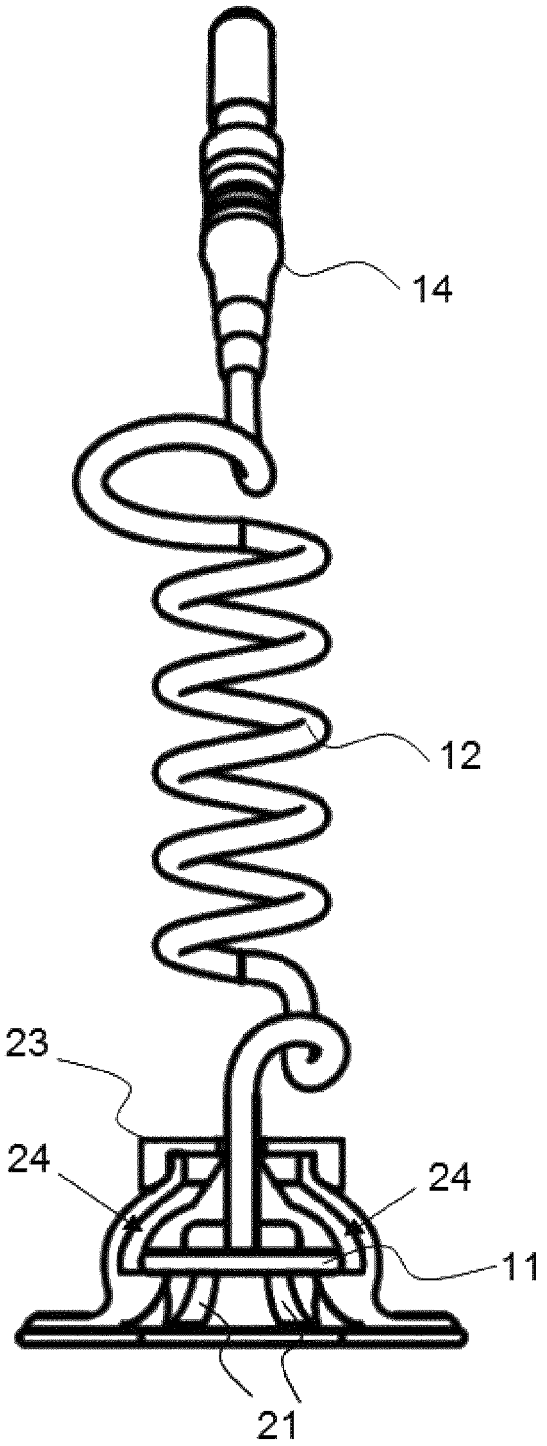
Figure 5C:
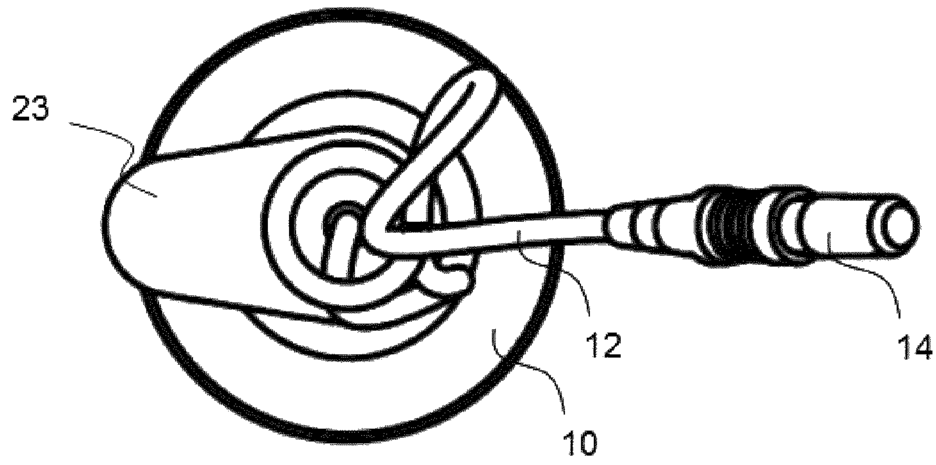
Figure 5D:
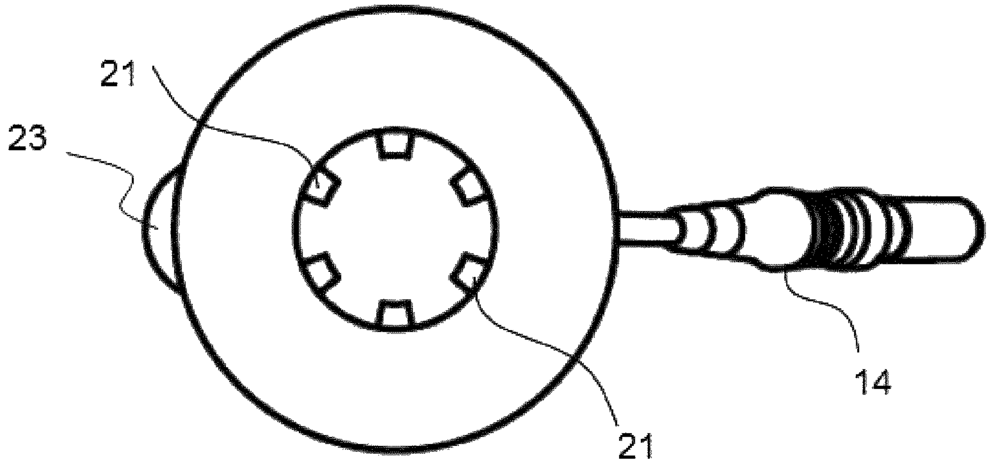
Figure 5E:
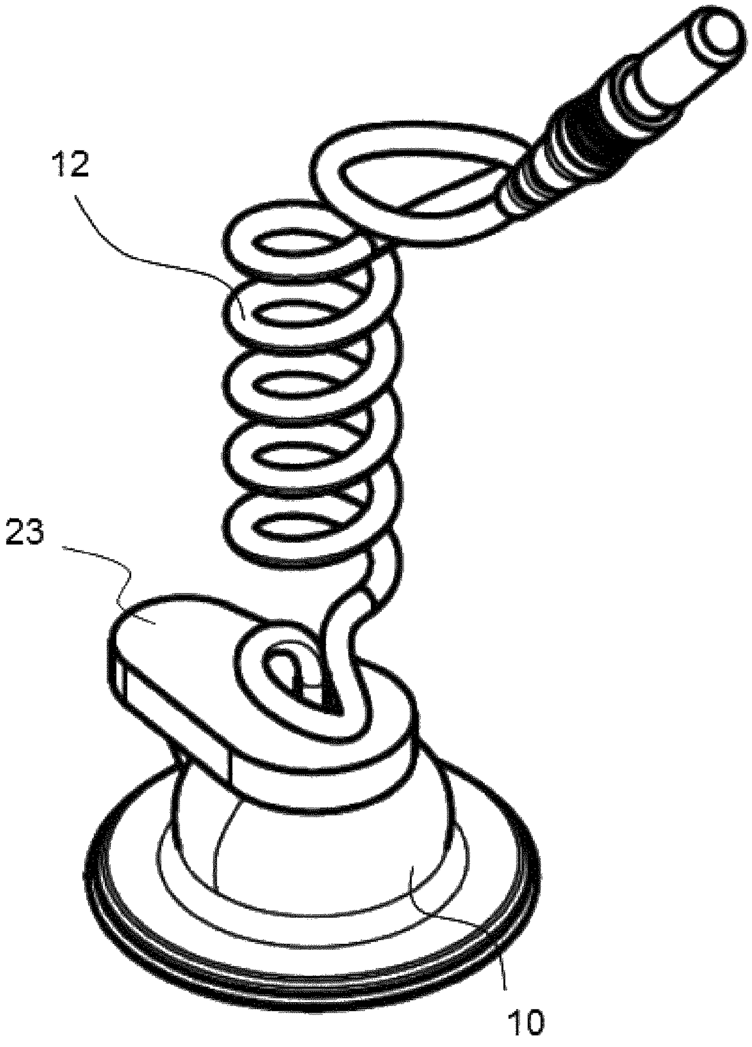

FIGS. 4A and 4B illustrate another embodiment in which the bottom surface 10C of the housing 10 is curved. In this embodiment, the adhesive element comprises a double-sided tape 13B and the electrode plate 11 is not pierced.

In some embodiments, sealing elements can be also disposed between the housing 10 and the insulating layer 18 of the wire connection 12. In some embodiments also, the first protruding part 16 can comprise a plug for closure thereof.

With regard to FIGS. 5A-5E, therein another embodiment of the proposed electrode device 1 is shown. According to this embodiment, the wire connection 12 has a curved/spiral shape and the support surface comprises a plurality of supporting structures (or simply supports) 21 that hold the electrode plate 11. The electrode device 1 (see the two different sections of FIGS. 5A and 5B) also has an encapsulating element 22 positioned on top of the electrode plate 11 that isolates the wire-plate connection for the electroconductive gel. A gap 24 between the encapsulating element 22 and the housing 10 allows the electroconductive gel to flow from the hollow space 19 between the electrode plate 11 and the skin to the second protruding part 17. A sealing element 23 is also included covering an upper part of the housing 10 and the first hole 15, such that drying of the gel is reduced. To replace the electroconductive gel, the sealing element 23 has to be lifted to release the first protruding part 16 to insert a blunt needle and to visually check the drain of the gel through the second protruding part 17.

Figure 6A:
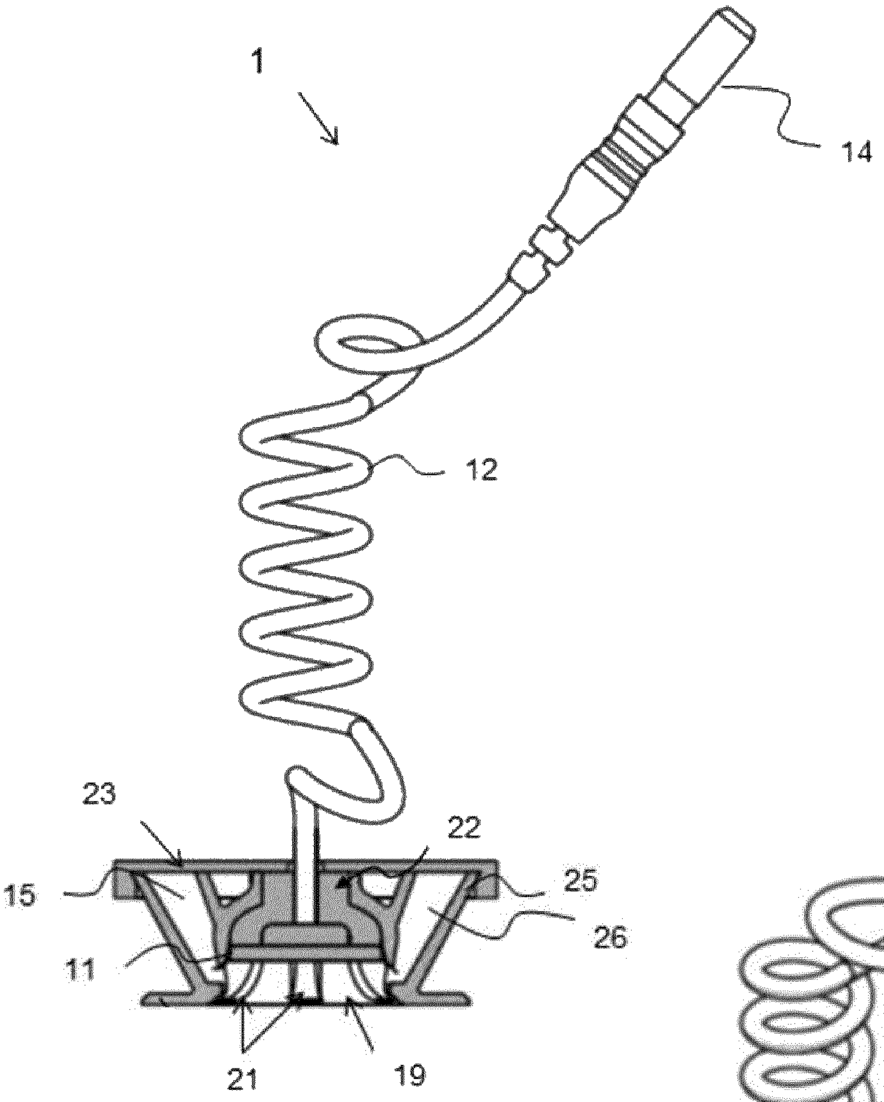
FIGS. 6A and 6B illustrate different views of another embodiment of the proposed electrode device.
Figure 6B:
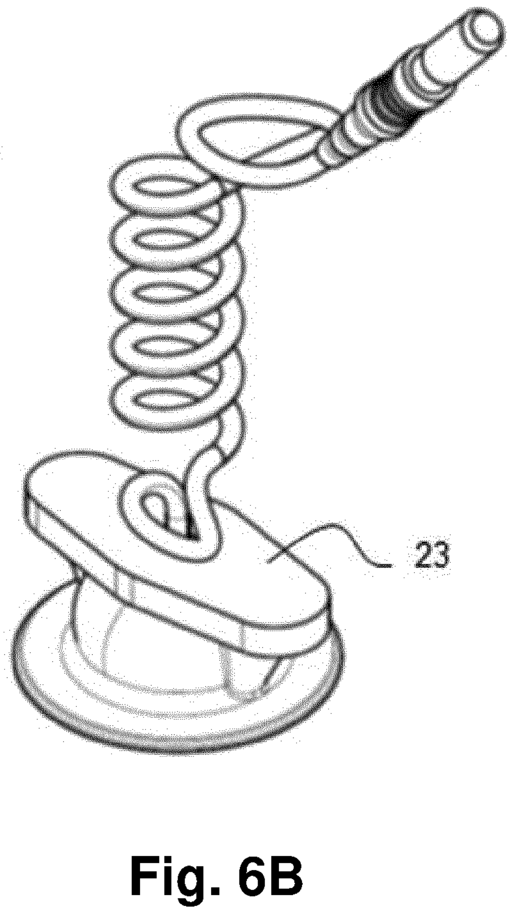

FIGS. 6A and 6B illustrate another embodiment of the proposed electrode device 1. The electrode device 1 of this embodiment is similar to the electrode device 1 of previous FIGS. 5A-5C but in this case the housing 10 besides the two protruding parts 16, 17 described above further has a (third) protruding part 25, which is symmetric to the protruding part 16. The protruding part 25 also includes a conical-shaped hole 26. The third protruding part 25 allows an easier replacement of the electroconductive gel in case the viscosity of the gel is too low, the gel used dries fast or in case the gel only remains in the bottom surface of the electrode plate 11. In this embodiment, to replace the electroconductive gel, after lifting the sealing element 23, a blunt needle can be inserted in the first 16 or third 25 protruding part and drained by the other one.

It will be understood that various details of the presently disclosed matter may be changed without departing from the scope of the presently disclosed matter. Furthermore, the previous description is for the purpose of illustration only, and not for the purpose of limitation.

As used herein, the term "about" and/or "substantially", when referring to a value or to feature, are meant to encompass variations of in some embodiment's ±10%, in some embodiment's ±5%, from the specified value or feature, as such variations are appropriate to perform the disclosed device.

The scope of the present disclosure is defined in the following set of claims.

The invention claimed is:

1. An electrode device for amplitude-integrated electroencephalography (aEEG) comprising:

a housing mounted on an adhesive element to adhere the electrode device to a skin surface of a patient;

an electrode plate placed in the housing at a certain distance from a support surface of the housing forming a hollow space; wherein the hollow space is configured to store an electroconductive gel between the electrode plate and the skin surface of a patient; and a wire connection for the electrode plate, said wire connection having a given length and comprising a proximal end and a distal end, wherein the housing comprises a first protruding part and a second protruding part, the first protruding part including a first hole, and the second protruding part including a second hole through which the proximal end of the wire connection is introduced and attached to the electrode plate, wherein the device further comprises a third protruding part that is symmetrically arranged with regard to the first protruding part, wherein the first protruding part is disposed in the housing inclined outwardly at an angle between 50-degree and 80-degree with respect to a contact surface of the electrode device, wherein the first hole has a conical-shaped geometry and is configured to periodically inject the electroconductive gel inside the hollow space by a pressure exerted by a blunt needle inserted into the first hole, wherein the third protruding part includes a conical-shaped hole configured to periodically drain and replace the electroconductive gel from the hollow space by the pressure exerted by the blunt needle, and wherein the housing comprises a shelf to sustain the electrode plate so that the first hole is connected to the hollow space and to the third hole.

2. The electrode device of claim 1, wherein the first protruding part is disposed at a 60 or 65 degree angle with respect to the contact surface of the electrode device.

3. The electrode device of claim 1, wherein the wire connection further comprises a connector on said distal end.

4. The electrode device of claim 1, wherein the adhesive element is a flexible adhesive pad comprising an adhesive layer provided on a lower surface thereof.

5. The electrode device of claim 1, wherein the adhesive element is a double-sided tape.

6. The electrode device of claim 1, wherein an attachment of the wire connection to the electrode plate comprises one or more welding points.

7. The electrode device of claim 1, wherein the length of the wire connection is less than 50 millimeters.

8. The electrode device of claim 1, wherein the length of the wire connection is between 0.5 and 2 meters.

9. The electrode device of claim 1, wherein the housing is made of a polymer, ceramic or metallic material; and wherein the electrode plate (11) is made of, or comprises a coating made of, Silver (Ag), Gold (Au), Silver/Silver-Chloride (Ag/AgCl), Tin, Stainless Steel, Platinum, Cooper, Lead, Nichrome, or a conductive non-magnetic polymer.

10. The electrode device of claim 1, wherein the first protruding part further comprises a plug for closure thereof.

11. The electrode device of claim 1, wherein a bottom surface of the housing configured to receive contact with the adhesive element has a given curvature.

12. The electrode device of claim 1, wherein the housing is made of a translucent and flexible material.

13. The electrode device of claim 1, wherein the wire connection has a spiral shape.

14. The electrode device of claim 1, wherein the support surface comprises a plurality of supporting structures configured to sustain the electrode plate, and the electrode device further comprises an encapsulating element positioned on top of the electrode plate.

15. The electrode device of claim 1, wherein the wire connection further comprises an insulating layer.

16. The electrode device of claim 15, wherein the insulating layer is made of a material comprising silicone, Polyvinyl chloride, Polyethylene, Polyvinylidene fluoride and/or Polypropylene.

17. The electrode device of claim 15, further comprising one or more sealing elements disposed either between the housing and the insulating layer of the wire connection or over the housing and the first protruding part.

* * * * *